United States Patent [19]
Dyer et al.

[11] Patent Number: 5,142,750
[45] Date of Patent: Sep. 1, 1992

[54] ABSORBENT WOUND DRESSING

[75] Inventors: John Dyer, Randolph; Grace Mathews, Princeton; Matthew M. Major, Sayreville, all of N.J.

[73] Assignee: Johnson & Johnson Medical, Inc., Arlington, Tex.

[21] Appl. No.: 648,501

[22] Filed: Jan. 30, 1991

Related U.S. Application Data

[62] Division of Ser. No. 304,156, Jan. 31, 1989, Pat. No. 5,062,418.

[51] Int. Cl.⁵ .................... D06C 11/00; D04H 1/06
[52] U.S. Cl. ........................................ 26/29 R; 28/103
[58] Field of Search ........................ 26/29 R; 28/103

[56] References Cited

U.S. PATENT DOCUMENTS

| | | | |
|---|---|---|---|
| 4,480,362 | 11/1984 | Maxwell | 26/28 |
| 4,555,430 | 11/1985 | Mays | 28/103 |
| 4,797,311 | 1/1989 | Kemp | 26/29 R |

FOREIGN PATENT DOCUMENTS

| | | | |
|---|---|---|---|
| 2742761 | 3/1978 | Fed. Rep. of Germany | 26/29 R |
| 47-17743 | 5/1972 | Japan | 26/29 R |

OTHER PUBLICATIONS

New Techniques in Fabric Raising, Knitting Times, Jul. 9, 1979 vol. 48, No. 29 pp. 11–13.

*Primary Examiner*—Werner H. Schroeder
*Assistant Examiner*—John J. Calvert

[57] ABSTRACT

A soft, bulky light weight fabric having good absorbency and suitable for use as a wound dressing is prepared from a hydroentangled nonwoven fabric comprising a plurality of parallel spaced apart ribs interconnected by loose fiber bundles extending between adjacent ribs. The ribs comprise high density, highly entangled masses of fibers and contain at least about 60 percent by weight of the fiber in the fabric. The fabric is napped in a direction perpendicular to the ribs to obtain the soft, bulky fabric without tearing or disrupting the integrity of the fabric.

5 Claims, 4 Drawing Sheets

ABSORBENT WOUND DRESSING

This is a division of application Ser. No. 07/304,156, filed Jan. 31, 1989, now U.S. Pat. No. 5,062,418.

FIELD OF INVENTION

This invention relates to wound dressings comprising fibrous materials, and more particularly to highly absorbent wound dressings comprising a soft, bulky, nonwoven fabric.

BACKGROUND OF THE INVENTION

Wound dressings are used to clean, cover and protect wounds in order to facilitate the healing thereof. Absorbent wound dressings remove wound exudate, providing a clean, dry environment to promote healing while protecting the wound from the external environment. Absorbent wound dressings may also be used as wipes or swabs to cleanse skin, clean wounds or apply medicaments.

Wound dressings have customarily been made from textile fabrics such as woven gauze. The low absorbent capacity and low bulk of woven gauze required the use of multiple layers of folded material to achieve adequate performance. Disadvantages in the use of gauze as a direct wound covering were recognized in its relatively poor absorbency, lack of bulk and poor wound release characteristics.

Since the development of nonwoven technology beginning in the early 1950's, gauze dressings have been progressively replaced by nonwoven products. The nonwoven fabrics are superior to gauze in the areas of absorbent capacity, conformability, bulk, softness and low linting. Because of the superior absorbency, fewer layers of nonwoven material were required to construct a dressing having an absorbent capacity matching or exceeding that of the gauze counterpart. Thus, a 4-ply nonwoven sponge would effectively replace a 12-ply or 16-ply gauze sponge in most applications.

Because the nonwoven dressing required fewer layers of fabric for the desired degree of absorbency, lightweight wound dressings of 2- or 4-ply fabric often lacked the degree of bulk associated with 12- or 16-ply woven gauze. Thus the full benefit of the nonwoven product in protecting and cushioning the wound was not realized. To achieve higher bulk without increasing the amount of nonwoven material used in the dressings, some wound dressings were assembled with an outer cover of nonwoven fabric enclosing an inner filler of cellulosic tissue or carded staple fiber. Such combination products provided increased bulk and absorbency while retaining the advantages of a low linting, nonwoven fabric on the outer surface.

The present invention is directed to a nonwoven fabric having improved bulk, softness and absorbency for a given weight and construction. The present invention is also directed to the method for preparing such nonwoven fabrics and to wound dressings comprising such nonwoven material. These and other objects of the present invention will become apparent from the ensuing description and claims.

SUMMARY OF THE INVENTION

The nonwoven fabrics of the present invention which are uniquely well suited for use as wound dressings are prepared by subjecting a particular lightweight, hydroentangled nonwoven fabric to a napping process which enhances the bulk and softness of the fabric. The particular nonwoven fabric which comprises the starting material for the practice of the present invention is characterized by a repeating pattern of spaced, parallel, high-density rows of highly entangled fibers interconnected by spaced bundles of loosely entangled low-density fiber segments which are substantially parallel to each other and perpendicular to the high-density rows of highly entangled fibers.

Nonwoven fabrics having the particular structure required for the present invention are described in U.S. Pat. Nos. 4,379,799; 4,465,726; 4,693,922 and 4,735,842, all of which are incorporated herein by reference for their teachings in connection with the fabrics and their method of manufacture. These fabrics are produced by a process which involves, in brief, supporting a layer of staple length fibers on a porous forming belt of a specific construction and subjecting the fibers to streams of high pressure, fine and essentially columnar jets of water as the forming belt and fibers move through an entangling zone.

The nonwoven fabric resulting from the entanglement of the staple length fibers is removed from the supporting belt, a resin binder is optionally applied and the fabric is dried in an oven or over steam cans. The resulting fabric has the typical appearance of ribbed terry cloth characterized by a repeating pattern of spaced, parallel, raised, high-density ribs extending across the width of the fabric in the cross-direction. The raised ribs are interconnected by valleys comprising low-density bundles of lightly entangled fibers extending in the machine direction. The low-density fiber bundles are spaced apart and provide a series of apertures in the valleys between the ribs.

The dried fabric may have a weight of from about 1 to 6 oz. per square yard with weights of from about 1.2 to 2.5 being particularly preferred for the present invention. In accordance with the present invention, the dried fabric is further processed through a napping apparatus wherein the fabric is passed over several cylinders covered by wire pins. Alternating cylinders rotate in the same direction but with surface speeds which are either higher or lower than the speed of the fabric so that while one cylinder raises the fibers in one direction, the following cylinder raises and combs the fibers in the opposite direction. The direction of cylinder rotation is parallel to the machine direction of the cloth so that the action of the cylinders is concentrated on the high density ribs extending in the cross-direction of the fabric. The napping action has little effect on the lightly entangled fiber bundles extending between the ribs in the machine direction of the fabric.

The napped fabric has increased bulk, softness and absorbency as compared to the unnapped fabric while retaining good strength in both the machine and cross-directions. The fabric may be napped on one or both sides. For surgical applications where low linting is particularly important, the fabric is napped on one side only, and the napped side is folded to the inside of the final dressing where it provides bulk and softness to the dressing, while the outer face of the dressing comprises the unnapped, low linting surface of the fabric.

DETAILED DESCRIPTION OF INVENTION

Figure 1:
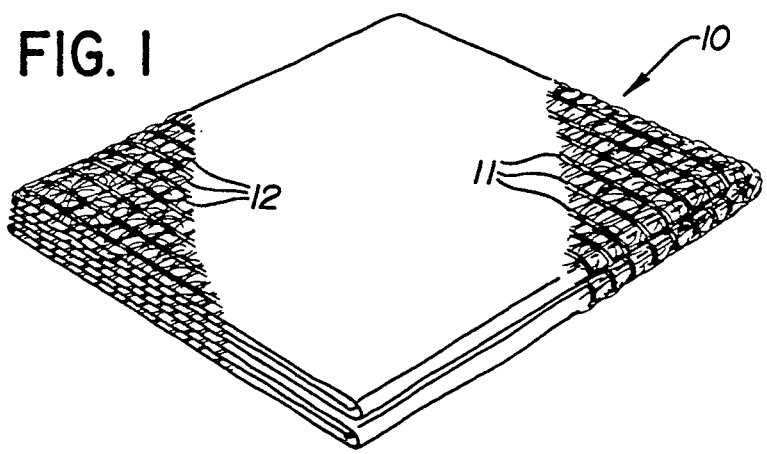
FIG. 1 is a perspective view of a folded wound dressing comprising the fabric of this invention.

The fabrics useful in the practice of the present invention may be prepared according to the process described in U.S. Pat. No. 4,379,799 with particular reference to the forming belts illustrated in FIGS. 16-18 thereof and the resulting fabrics of FIGS. 19-22. The fabrics, which preferably have a basis weight of at least 1.0 oz/yd$^2$, can be formed of a wide variety of staple textile fibers and preferably comprise rayon or cotton or mixtures of these with polyester, nylon, acrylics or the like. The staple fibers are preferably from 1 to 3 denier and have a staple length of from 1 to 2 inches.

In the following examples, fabrics were prepared from a blend of 75% by weight polyester and 25% by weight rayon staple fibers. The rayon fibers were nominally 1.5 denier with a staple length of 1.25 inches and approximately 16 crimps per inch. The polyester fibers were nominally 1.5 denier, with a staple length of 1.5 inches and approximately 12 crimps per inch. The blended staple fibers were processed into light weight card (oriented) and isocard (randomized) webs, which were combined in a ratio of ⅓ card web and ⅔ isocard web by weight. The combination web was then converted to a nonwoven fabric by hydroentangling according to the method of U.S. Pat. No. 4,379,799. Approximately 3.5 to 4 percent by weight of acrylic resin binder was applied to the nonwoven fabric.

The process and apparatus for forming the nonwoven fabrics useful in the practice of the present invention are described in U.S. Pat. No. 4,379,799 as follows:

"The fabric of the invention is produced by a process which comprises:
(a) supporting a layer of fibrous starting material whose individual fibers are in mechanical engagement with one another but which are capable of movement under applied liquid forces, on a liquid pervious support member adapted to move in a predetermined direction and on which fiber movement in directions both in and at an angle to the plane of said layer is permitted in response to applied liquid forces, said support member having alternating liquid impervious deflecting zones and liquid pervious entangling zones extending transversely to said predetermined direction, said deflecting zones including spaced deflecting means adapted to deflect liquid in a direction transverse to said predetermined direction;
(b) moving the supported layer in said predetermined direction through a fiber rearranging zone within which streams of high pressure, fine, essentially columnar jets of liquid are projected directly onto said layer; and
(c) passing said stream of liquid through said layer and said support member in said fiber rearranging zone to effect such movement of fibers such that (1) spaced bundles of straight, substantially parallel fiber segments are formed in said deflecting zones, said bundles being oriented generally in said predetermined direction, (2) spaced, parallel ribs are formed in said entangling zones, said ribs extending in a direction transverse to said predetermined direction, and said ribs comprising entangled fibers that are substantially wholly entangled throughout said ribs, and (3) said spaced bundles interconnect said ribs and are locked into said ribs at the ends of said bundles by fiber entanglement.

"The apparatus for producing the fabric of the invention comprises:
(a) liquid pervious forming means for supporting a layer of fibrous starting material whose individual fibers are in mechanical engagement with one another but which are capable of movement under applied liquid forces;
(b) means for projecting streams of high pressure, fine, essentially columnar jets of liquid; and
(c) means for passing said layer of fibrous starting material directly under said streams while said layer is supported on said liquid pervious forming means, wherein said liquid pervious forming means comprises a woven belt having first fine threads in one fabric direction, and heavier threads and second fine threads in the other fabric direction, the belt having a topography such that there are raised parallel ridges alternating with depressions, wherein each raised ridge comprises one of said heavier threads, wherein said first fine threads pass over said heavier threads at spaced intervals, and wherein said depressions include said first fine threads interlaced with said second fine threads, The belt is relatively tightly woven so that the fibers in said layer will not tend to wash through the belt and so that the ribs which form in the depressions are non-apertured and, at least macroscopically, are substantially uniform and substantially non-patterned."

The fabrics useful in the practice of the present invention are characterized by spaced parallel ribs of high density, highly entangled fibers extending in the cross direction of the fabric. In a typical fabric, there are from 5-10 ribs per inch. The ribs comprise about one-third the surface area of the fabric and at least about 60% by weight of all the fiber in the fabric is contained in the rib area. The ribs are interconnected by spaced bundles of lightly entangled fibers which form an apertured low density area of the fabric and usually contain less than 40% of the total fiber content of the fabric. Analysis of a specific fabric sample having a basis weight of approximately 1.2 oz/yd$^2$ and approximately 8 ribs per inch found 64-68% of the fiber contained in the rib area and 32-36% of the fiber content in the area between the ribs, with the space between adjacent ribs being approximately twice the width of the individual ribs.

In the napping process, the napping wires are oriented on cylinders in a direction parallel to the direction of rotation, and thus move parallel to the machine direction of the fabric. In this configuration, the pins of the wire pass easily between the fiber bundles in the valleys of the fabric which are oriented in the machine direction leaving them substantially undisrupted. The napping action is primarily achieved through contact of the napping wires with the raised rib areas of the fabric which run transversely throughout the fabric in the cross direction and are substantially perpendicular to the direction of rotation of the napping wires.

In the following examples, fabrics were napped on a Lamperti Napper GB/L 84 manufactured by Lamperti, Busto Arsizio, Italy, following the manufacturers operating instructions. The energy levels for the pile and counterpile rollers are adjusted as necessary to achieve the desired napping effect without seriously degrading the physical properties of the fabric. Table I provides details of single and multiple pass processing conditions with the Lamperti Napper for two ranges of fabric weight. The fabric was processed at 15 meters/minute. The data in Table I show revolutions per minute for the pile and counterpile rollers, and these values reflect energy being imparted to the fabric by the napping action. Increasing RPM values results in decreasing energy for the pile rollers and increasing energy for the counterpile rollers. To avoid excessive degradation of the fabric with multiple passes, the roller settings are adjusted to lower energy levels as the number of passes is increased.

TABLE I

| | Napping Process Conditions | | | | | | |
|---|---|---|---|---|---|---|---|
| Sample | Fabric Basis Weight | Treat-ment[1] | 1st Pass[2] | | 2nd Pass | | 3rd Pass | |
| | | | p | cp | p | cp | p | cp |
| 1 | 2.0 oz/yd² | B | 796 | 876 | — | — | — | — |
| 2 | 2.3 | B-J | 776 | 574 | 772 | 576 | — | — |
| 3 | 2.4 | B-B-J | 790 | 548 | 798 | 546 | 760 | 566 |
| 4 | 1.5 | B | 802 | 872 | — | — | — | — |
| 5 | 1.4 | J-B | 796 | 532 | 746 | 560 | — | — |
| 6 | 1.5 | B-B-J | 792 | 536 | 816 | 524 | 796 | 532 |

[1]Treatment - B = belt side of fabric
J = jet side of fabric
[2]p = pile roller RPM
cp = counterpile roller RPM Table II presents data on the tensile and burst strengths of the fabric samples of Table I. Tensile strength was determined according to ASTM-D1682 for grab tensile strength. According to this method, a 4"×6" sample held by 1" clamps is broken in both the machine direction (MD) and cross direction (CD). The resulting breaking strength in pounds was divided by the unit basis weight of the fabric and expressed as tenacity for purposes of comparison in Table II. Burst strength was determined according to ASTM-3786. According to this method, bursting strength is reported as the pressure in pounds per square inch required to produce a rupture of the material when the pressure is applied at a controlled increasing rate through a rubber diaphragm to a circular area of the sample. The burst strengths are also normalized in Table II to the unit weight of the fabric for purposes of comparison.

TABLE II

| | | Fabric Strength | | | | | |
|---|---|---|---|---|---|---|---|
| | | Tenacity[3] | | | | Burst Strength[4] | |
| | Basis[2] | Dry | | Wet | | | |
| Sample[1] | Weight | MD | CD | MD | CD | Dry | Wet |
| C-1 | 2.6 | 13.4 | 10.5 | 13.9 | 10.5 | 24.3 | 24.8 |
| 1 | 2.0 | 6.8 | 5.2 | 6.5 | 4.6 | 17.5 | 14.9 |
| 2 | 2.3 | 5.7 | 3.0 | 4.5 | 3.5 | 17.8 | 18.6 |
| 3 | 2.4 | 7.7 | 4.4 | 7.1 | 4.3 | 14.6 | 16.9 |

TABLE II-continued

| | | Fabric Strength | | | | | |
|---|---|---|---|---|---|---|---|
| | | Tenacity[3] | | | | Burst Strength[4] | |
| | Basis[2] | Dry | | Wet | | | |
| Sample[1] | Weight | MD | CD | MD | CD | Dry | Wet |
| C-2 | 1.5 | 13.7 | 11.0 | 12.2 | 10.2 | 26.0 | 23.4 |
| 4 | 1.5 | 6.9 | 4.0 | 6.6 | 4.0 | 13.7 | 17.8 |
| 5 | 1.4 | 8.7 | 5.1 | 7.1 | 4.5 | 15.4 | 14.2 |
| 6 | 1.5 | 12.1 | 4.8 | 11.0 | 4.2 | 19.9 | 21.0 |

[1]C-1 = control
C-2 = control
[2]Basis weight = oz/yd²
[3]Tenacity = Tensile Strength (lbs)/Basis Weight (oz/yd²)
[4]Burst Strength = psi per oz/yd²

As seen from the data in Table II, processing the fabric in accordance with the present invention results in a sizeable decrease in both tensile strength and burst strength. Nevertheless, the napped fabric maintains its structural integrity, i.e. there are no ruptures or tears in the fabric as a result of the napping process, and the fabric retains more than adequate strength for use as a surgical sponge or cleansing wipe.

Table III presents averaged data on the bulk and absorbency of four fabrics having basis weights from 1.2 to 2.5 oz/yd². Bulk was determined by measuring the thickness of a four-ply folded dressing under a weight of 2 ounces on a presser foot one inch in diameter. Absorbent capacity was determined by the Gravimetric Absorbency Test (GAT) method and by the dip/drip method using saline as the test liquid. In the GAT method, the amount of liquid absorbed is determined gravimetrically on an apparatus which maintains a constant level of source liquid delivered to a fabric sample supported on an apertured plate at the same level as the source liquid. Liquid absorption is a direct function of the ability of the fabric to draw liquid from the orifice at zero head. The apparatus and method are more fully described in "Absorbency", Textile Science and Technology, Volume 7, page 67, edited by P. K. Chatterjee and published by Elsevier, 1985.

In the dip/drip method of determining saturation absorbent capacity, a weighed, folded sponge is placed on the surface of the liquid contained in a tray and allowed to submerge. Ten seconds after submerging, the sample is removed using a forceps to grip one corner and allowed to drip for one minute. The wet weight of the sponge is then measured and the amount of absorbed fluid calculated. The saturation capacity is expressed as grams of fluid per gram of dry sponge weight.

TABLE III

| | Bulk and Absorbent Capacity | | | |
|---|---|---|---|---|
| SAM-PLE | PROPERTY | PLAIN | NAPPED | % INCREASE |
| 7 | Basis weight, oz/yd² | 1.19 | 1.15 | — |
| | Bulk, 4 ply (in.) | .053 | .113 | 113.2 |
| | Absorbency GAT. (g/g) | 8.34 | 16.21 | 94.4 |
| | dip/drip (g/g) | 7.84 .0445 7.01 | 17.05 .0982 14.1 | 117.5 |
| 8 | Basis weight, oz/yd² | 1.53 | 1.55 | — |
| | Bulk, 4 ply (in.) | .082 | .151 | 84.1 |
| | Absorbency GAT. (g/g) | 10.00 | 15.98 | 59.8 |
| | dip/drip (g/g) | 9.87 .0536 6.54 | 16.46 .097 10.3 | 66.8 |

TABLE III-continued

| | | Bulk and Absorbent Capacity | | |
|---|---|---|---|---|
| SAMPLE | PROPERTY | PLAIN | NAPPED | % INCREASE |
| 9 | Basis weight, oz/yd² | 1.98 | 1.96 | — |
| | Bulk, 4 ply (in.) | .107 | .176 | 64.5 |
| | Absorbency GAT. (g/g) | 8.45 | 15.55 | 84.0 |
| | dip/drip (g/g) | 8.11 | 16.19 | 99.6 |
| | | .054 | .090 | |
| | | 4.27 | 7.93 | |
| 10 | Basis weight, oz/yd² | 2.58 | 2.46 | — |
| | Bulk, 4 ply (in.) | .119 | .211 | 77.3 |
| | Absorbency GAT. (g/g) | 7.62 | 14.81 | 94.4 |
| | dip/drip (g/g) | 7.33 | 15.19 | 107.2 |
| | | .040 | .086 | |
| | | 2.95 | 6.02 | |

As seen from the data in Table III, the bulk of a 4 ply fabric structure and its absorbent capacity are substantially increased by the napping process. These two properties are very important for wound dressings and wipes, and the substantial increase in these properties represent a significant improvement in the product.

As might be expected, it is easier to remove fibers from the surface of the napped fabric of the present invention than from the original nonwoven fabric as a consequence of the napping operation raising and loosening fibers from the tightly compacted structure in the ribs of the fabric. The integrity of the fabric surface is evaluated by a comparative adhesive pull-off test wherein a weighed piece of pressure sensitive adhesive tape is applied to the surface of the product, then peeled off and reweighed to determine the amount of fiber pickup. The results of this test are presented in Table IV.

TABLE IV

| | | Fiber Pull-off, mg. Fiber | | |
|---|---|---|---|---|
| | Fabric Basis | | Napping Treatment[1] | |
| Sample | Weight | None | B | B-J | B-B-J |
| 11 | 1.2 oz/yd² | 0.3/0.4[2] | 3.3/1.8 | — | — |
| 12 | 1.5 | 0.3/0.5 | 8.9/0.7 | 5.0/6.7 | 4.5/1.9 |
| 13 control[3] | 2.5 | 0.3/0.4 | 10.4/0.6 | 7.4/4.8 | 13.4/7.6 |
| | — | 1.3 | | | |

[1] B = Napped belt side only
B-J = Napped belt side and jet side
B-B-J = Napped twice on belt side, once on jet side
[2] Fiber pull-off (mg.), Belt side/Jet side
[3] Control = commercial folded gauze pad As seen from the data in Table IV, fiber pull-off values are primarily affected on the side of the fabric which is subjected to the napping process. Where only the belt side of the fabric was napped, there is no significant change in fiber pull-off values on the unnapped jet side of the fabric for either the 1.5 or the 2.5 ounce fabrics. Only the very lightweight 1.2 ounce fabric showed a significant increase in jet side fiber pull-off. Where linting may be of concern, as for example, in a surgical wound dressing, bulk and absorbency of the nonwoven fabric may be significantly increased without increasing the linting problem by napping the fabric on one side only, and folding that side into the center of the sponge so that the unnapped side forms the outer surface. In other applications where linting is of no concern, as in swabs and wipes for cleansing skin, the fabric may be napped on both sides to maximize bulk, softness and absorbency.

Figure 2:
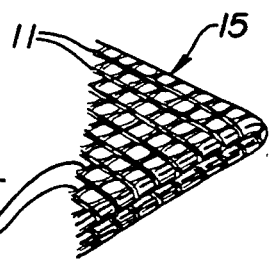
FIG. 2 is a partial perspective view of a folded wound dressing comprising an unnapped, nonwoven fabric.

Referring now to the figures of the present invention, FIG. 1 illustrates a folded 3×3 inch wound dressing (10) formed of a napped nonwoven fabric of the present invention. FIG. 2 is a partial view of a folded wound dressing (15) formed of the same nonwoven fabric as that of FIG. 1, except that the fabric had not been napped according to the present invention. The fabrics of FIG. 1 and FIG. 2 each have a structure which is characterized by a repeating pattern of spaced, parallel, raised ribs (11) which extend continuously in the cross direction of the fabric. The ribs are interconnected by spaced bundles (12) of straight substantially parallel fiber segments, with said bundles being substantially parallel to one another and substantially perpendicular to said ribs. Adjacent bundles and the ribs they interconnect define a series of apertures in the fabrics. The fibers in the ribs (11) are highly entangled throughout and on a macroscopic scale, the ribs appear uniform and substantially nonpatterned.

Figure 3:
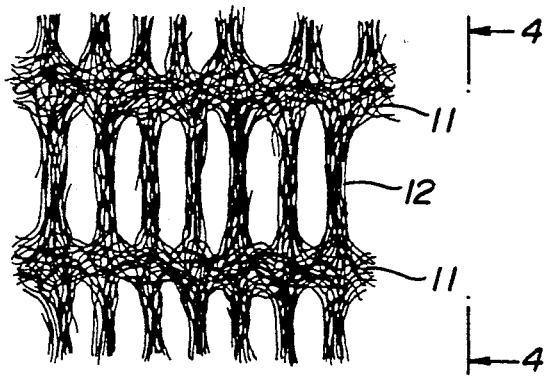
FIG. 3 is a plan view of the fabric used in the present invention before napping in an enlarged artistic representation.
Figure 4:
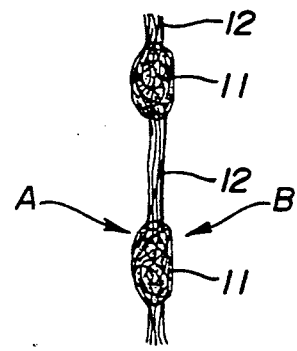
FIG. 4 is an end view of the fabric of FIG. 3.

The fabric structure is illustrated in greater detail in the artistic renditions of FIGS. 3–6 wherein FIG. 3 is a plan view of the unnapped fabric showing highly entangled, high density ribs (11) interconnected by fiber bundles (12) which extend substantially perpendicular to ribs (11). As illustrated, ribs (11) extend in the cross direction of the fabric and fiber bundles (12) extend in the machine direction. The ribs are more prominent on side A which is the belt side of the fabric, than on side B which is the jet side. FIG. 4 presents a side view of the fabric of FIG. 3 and more clearly illustrates the fiber density in the rib area and the interconnecting valley areas between the ribs.

Figure 5:
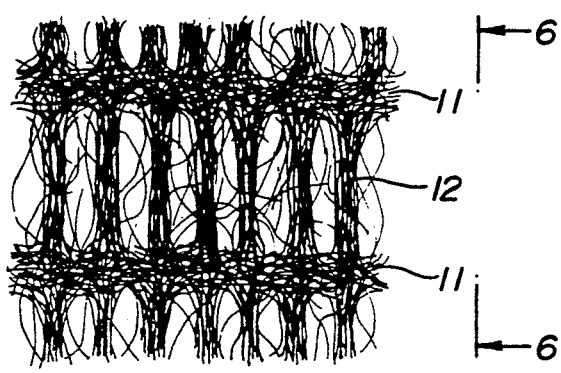
FIG. 5 is a plan view of the fabric of FIG. 3 after napping.
Figure 6:
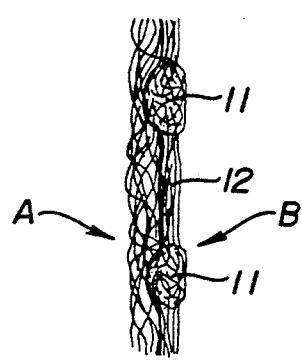
FIG. 6 is an end view of the fabric of FIG. 5.

FIGS. 5 and 6 are corresponding plan and end views of the fabric of FIGS. 3 and 4 after napping on the belt side only. During the napping process, the fabric is subjected to the pins of the napping rolls which are rotating parallel to the machine direction of the fabric. As a consequence, the pins of the napping rolls pass readily through fiber bundles (12) wherein the individual fibers are substantially oriented in the machine direction of the fabric. Thus the napping process has little direct effect on the bundle portions of the fabric, although the fibers may be separated to some degree.

The napping process acts primarily on ribs (11) which extend in the cross direction of the fabric and are generally perpendicular to the direction of rotation of the pin rolls. As the pin rolls pass over the ribs, they lift and pull fiber ends free from the highly compacted rib area, and direct the fibers into the valleys between the ribs. The result is a great softening of the ribs and a significant increase in fabric bulk in the rib area and in the valley area between ribs.

Figure 7:
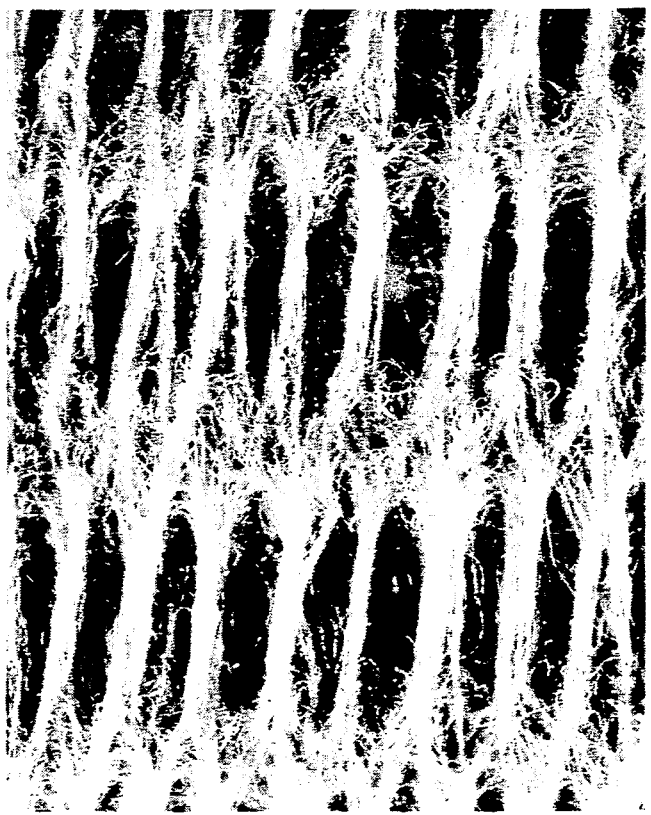
FIG. 7 is a 10× photomicrograph of an actual fabric utilized in the present invention before napping.
Figure 8:
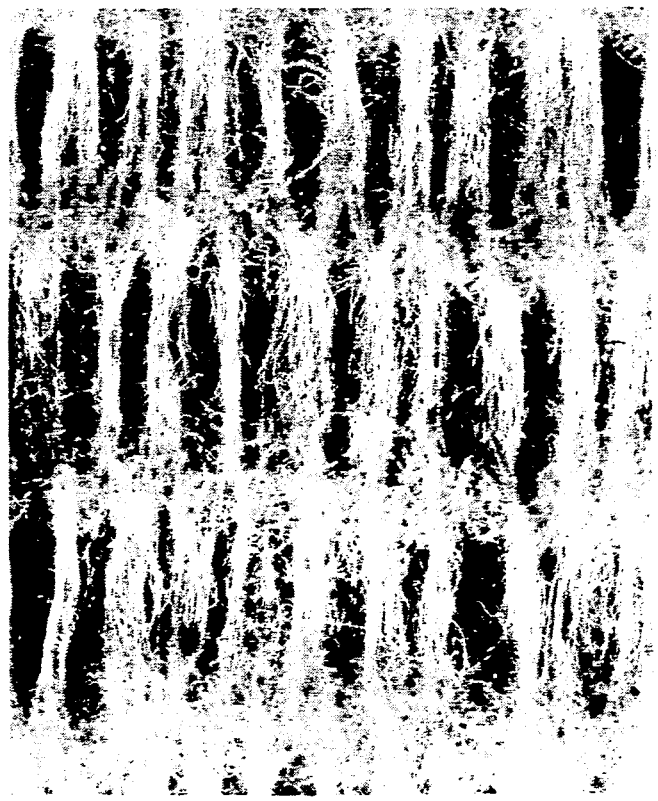
FIG. 8 is a 10× photomicrograph of the fabric of FIG. 7 after napping.

FIGS. 7 and 8 are 10× photomicrographs of an actual nonwoven fabric before and after napping in accordance with the present invention. While the photos do not give a good indication of fabric bulk, it can be seen in FIG. 8 that the fiber bundles extending between and interconnecting the ribs of the fabric maintain their integrity and are not significantly disrupted by the nappinq process even though they are less compact than in the original structure of FIG. 7.

Figure 9:
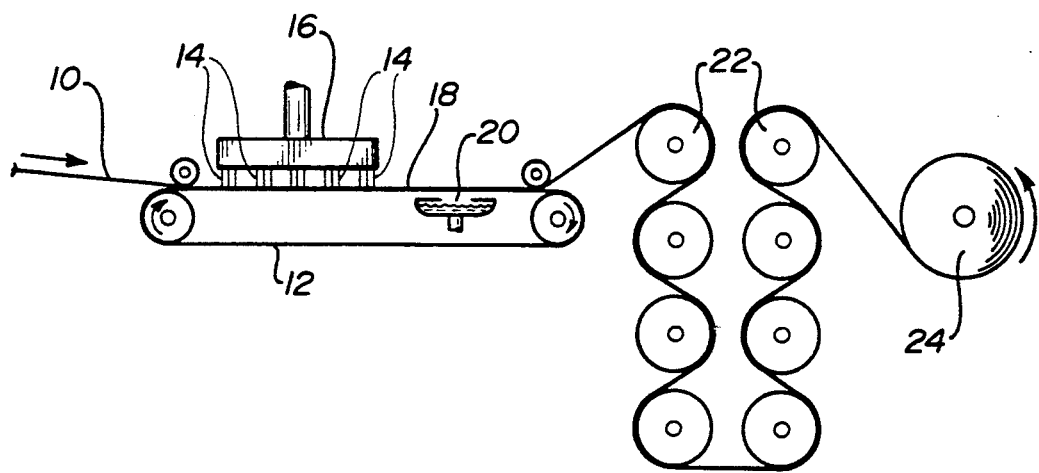
FIG. 9 is a schematic side elevation of an apparatus that is used to prepare fabrics useful in the practice of the present invention.

The nonwoven fabric used in the method of this invention is produced by the fluid rearrangement/entanglement of a web comprising a loose array of fibers, on a liquid pervious woven forming belt. Referring to FIG. 9, a carded or random laid web 10 of staple fibers is passed onto an endless belt 12, which is the woven forming belt. The belt 12 carries the web of fibers 10 under a series of high pressure fine, essentially columnar jets of water 14. The high pressure water is supplied from a manifold 16. The jets 14 are arranged in rows disposed transversely across the path of travel of the forming belt 12. Preferably, there is a vacuum slot (not shown) pulling a vacuum of, e.g., 5 to 15 inches of mercury, beneath the forming belt 12, directly under each row of jets 14, in order to optimize durability of the fabric product. The fibers in the web 10 are rearranged and entangled by the jets 14 as the liquid from the jets 14 passes through the fibrous web 10 and then through the belt 12, to form the fabric 18. The fabric 18 is carried by the belt 12 over a vacuum dewatering station 20, and then proceeds to a series of drying cans 22, and from there to a windup 24.

Figure 10:
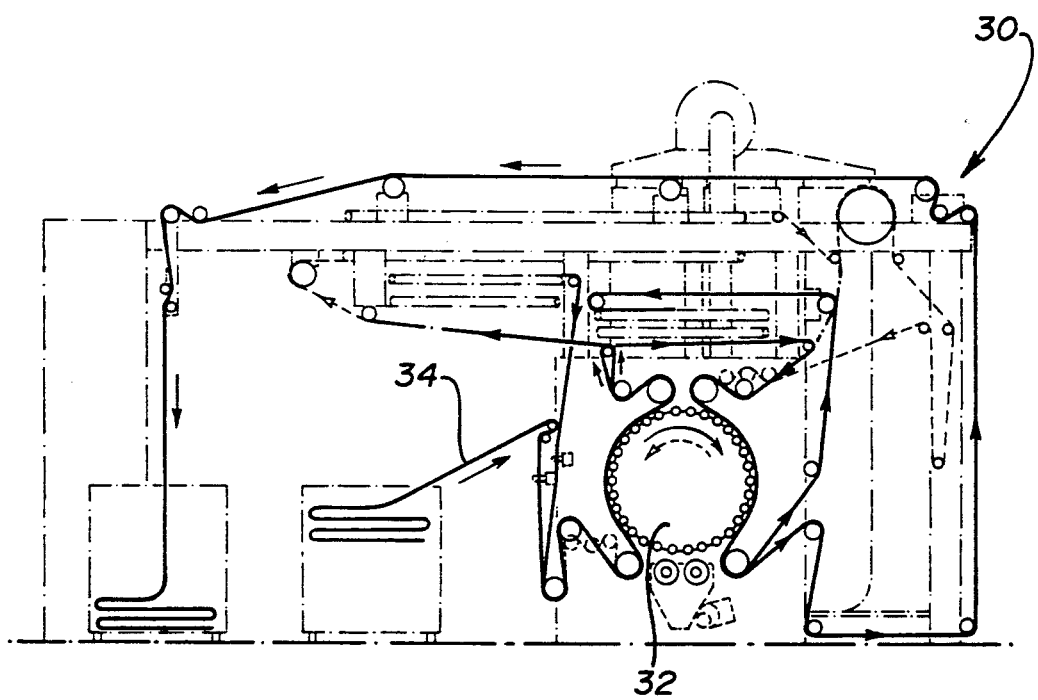
FIG. 10 is a schematic of a napper suitable for the method of the present invention.

A schematic of the napping process is shown in FIG. 10, which shows napper 30 (Lamberti Napper GB/L84), including napping cylinder 32, fabric 34, and the route followed by fabric 34 as it is napped.

The method of the present invention provides a new, bulky, highly absorbent material particularly well-suited for use as a wound dressing or cleansing wipe. While the invention has been described in conjunction with certain specific embodiments thereof, it is evident that many alternatives, modifications, and variations will be apparent to those skilled in the art in light of the above description. Accordingly, it is intended to embrace all such embodiments that fall within the spirit and broad scope of the appended claims.

We claim:

1. A method for producing a soft, bulky, highly absorbent nonwoven fabric comprising the steps of:
   a. supporting a layer of staple length fibers on a porous forming belt, whose long direction defines a machine direction, the belt having alternating liquid impervious deflecting zones and liquid pervious entangling zones extending transversely to the machine direction,
   b. moving the supported layer in the machine direction through a fiber rearranging zone within which streams of high pressure water are projected directly onto the layer.
   c. passing the streams of water through the layer and support member in the fiber rearranging zone to form a nonwoven fabric having a repeating pattern of spaced parallel ribs extending in the cross direction of said fabric, each of said ribs comprising a highly entangled fibrous mass, and a plurality of spaced parallel and substantially straight fiber bundles ending between and interconnecting adjacent ribs with said fiber bundles being oriented in the machine direction of said fabric and substantially perpendicular to said ribs,
   d. providing the fibers to the belt at a rate that will form fabric having a basis weight of from about 1.2 to 2.5 oz/yd$^2$, and
   e. subjecting said nonwoven fabric to a napping process on at least one side thereof, using a napping apparatus that comprises a plurality of napping wires, by directing the napping wires against the fabric in the machine direction of said fabric, said napping wires being substantially parallel to said fiber bundles and perpendicular to the ribs of said fabric, thereby raising and bulking the fibers in said rib areas of said fabric while leaving the fibers in said bundles extending between said ribs substantially undisrupted.

2. The method of claim 1 wherein said fabric is composed of a blend of rayon and polyester staple fibers.

3. The method of claim 2 wherein said staple fibers are from 1 to 3 denier, and have a staple length from 1 to 2 inches.

4. The method of claim 1 wherein said fabric comprises a blend of 25% by weight rayon and 75% by weight polyester staple fibers having a denier of about 1.5 and a staple length of about 1.25 inches.

5. The method of claim 1 wherein said nonwoven fabric contains at least about 60% by weight of total fiber mass in the ribs of said fabric.

* * * * *